(12) United States Patent  
Bange et al.

(10) Patent No.: US 8,639,339 B2  
(45) Date of Patent: *Jan. 28, 2014

(54) SYSTEM AND METHOD FOR RF WAKE-UP OF IMPLANTABLE MEDICAL DEVICE

(71) Applicant: Cardiac Pacemakers, Inc., St. Paul, MN (US)

(72) Inventors: Joseph E. Bange, Eagan, MN (US); Allan T. Koshiol, Lino Lakes, MN (US); Karen M. Kramer, Stillwater, MN (US); Paul Holmquist, Andover, MN (US); Thomas J. Harris, Bloomington, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 13/682,263

(22) Filed: Nov. 20, 2012

(65) Prior Publication Data

US 2013/0090705 A1    Apr. 11, 2013

Related U.S. Application Data

(63) Continuation of application No. 13/218,672, filed on Aug. 26, 2011, now Pat. No. 8,326,424, which is a continuation of application No. 12/102,480, filed on Apr. 14, 2008, now Pat. No. 8,024,043, which is a continuation of application No. 11/101,142, filed on Apr. 7, 2005, now Pat. No. 7,359,753.

(60) Provisional application No. 60/560,171, filed on Apr. 7, 2004.

(51) Int. Cl.
*A61N 1/08* (2006.01)

(52) U.S. Cl.
USPC .............................................. 607/32; 607/60

(58) Field of Classification Search
USPC ........................................................ 607/32, 60
See application file for complete search history.

(56) References Cited

U.S. PATENT DOCUMENTS 3,914,586 A   10/1975  McIntosh
4,341,982 A    7/1982  Lahti et al.
(Continued)

FOREIGN PATENT DOCUMENTS

DE      10119393 A1    1/2002
EP       0168640        1/1986
(Continued)

OTHER PUBLICATIONS

US 7,680,541, 3/2010, Von et al. (withdrawn).

(Continued)

*Primary Examiner* — Carl H Layno
*Assistant Examiner* — Jon Eric C Morales
(74) *Attorney, Agent, or Firm* — Schwegman Lundberg & Woessner, P.A.

(57) ABSTRACT

A telemetry system is presented for enabling wireless communications between an implantable medical device and an external device in a manner which reduces the power requirements of the implantable device by duty cycling its wireless communication circuitry. A wakeup scheme for the implantable device is provided in which the external device transmits a data segment containing a repeating sequence of special wakeup characters in order to establish a communications session with the implantable device. The wakeup scheme may be designed to operate in the context of a handshaking protocol for collision avoidance.

20 Claims, 2 Drawing Sheets

(56) References Cited

U.S. PATENT DOCUMENTS

| | | |
|---|---|---|
| 4,404,972 A | 9/1983 | Gordon et al. |
| 4,441,498 A | 4/1984 | Nordling |
| 4,486,739 A | 12/1984 | Franaszek et al. |
| 4,519,401 A | 5/1985 | Ko et al. |
| 4,539,992 A | 9/1985 | Calfee et al. |
| 4,542,532 A | 9/1985 | McQuilkin |
| 4,542,535 A | 9/1985 | Bates et al. |
| 4,543,954 A | 10/1985 | Cook et al. |
| 4,561,443 A | 12/1985 | Hogrefe et al. |
| 4,562,841 A | 1/1986 | Brockway et al. |
| 4,592,360 A | 6/1986 | Lesnick |
| 4,613,937 A | 9/1986 | Batty, Jr. |
| 4,634,294 A | 1/1987 | Christol et al. |
| 4,731,814 A | 3/1988 | Becker et al. |
| 4,799,059 A | 1/1989 | Grindahl et al. |
| 4,803,987 A | 2/1989 | Calfee et al. |
| 4,944,299 A | 7/1990 | Silvian |
| 4,945,909 A | 8/1990 | Fearnot et al. |
| 4,987,897 A | 1/1991 | Funke |
| 5,025,808 A | 6/1991 | Hafner |
| 5,074,308 A | 12/1991 | Sholder et al. |
| 5,080,096 A | 1/1992 | Hooper et al. |
| 5,089,019 A | 2/1992 | Grandjean |
| 5,109,853 A | 5/1992 | Taicher et al. |
| 5,113,869 A | 5/1992 | Nappholz et al. |
| 5,171,977 A | 12/1992 | Morrison |
| 5,230,003 A | 7/1993 | Dent et al. |
| 5,287,384 A | 2/1994 | Avery et al. |
| 5,292,343 A | 3/1994 | Blanchette et al. |
| 5,300,093 A | 4/1994 | Koestner et al. |
| 5,314,453 A | 5/1994 | Jeutter |
| 5,342,408 A | 8/1994 | deCoriolis et al. |
| 5,350,411 A | 9/1994 | Ryan et al. |
| 5,350,412 A | 9/1994 | Hoegnelid et al. |
| 5,370,666 A | 12/1994 | Lindberg et al. |
| 5,394,433 A | 2/1995 | Bantz et al. |
| 5,404,877 A | 4/1995 | Nolan et al. |
| 5,456,692 A | 10/1995 | Smith, Jr. et al. |
| 5,466,246 A | 11/1995 | Silvian |
| 5,476,488 A | 12/1995 | Morgan et al. |
| 5,486,200 A | 1/1996 | Lindemans |
| 5,516,285 A | 5/1996 | Yacker et al. |
| 5,532,708 A | 7/1996 | Krenz et al. |
| 5,535,752 A | 7/1996 | Halperin et al. |
| 5,562,713 A | 10/1996 | Silvian |
| 5,568,510 A | 10/1996 | Tam |
| 5,577,087 A | 11/1996 | Furuya |
| 5,579,876 A | 12/1996 | Adrian et al. |
| 5,593,430 A | 1/1997 | Renger |
| 5,598,847 A | 2/1997 | Renger |
| 5,603,331 A | 2/1997 | Heemels et al. |
| 5,617,871 A | 4/1997 | Burrows |
| 5,630,835 A | 5/1997 | Brownlee |
| 5,650,759 A | 7/1997 | Hittman et al. |
| 5,683,432 A | 11/1997 | Goedeke et al. |
| 5,694,952 A | 12/1997 | Lidman et al. |
| 5,697,958 A | 12/1997 | Paul et al. |
| 5,725,559 A | 3/1998 | Alt et al. |
| 5,729,680 A | 3/1998 | Belanger et al. |
| 5,733,313 A | 3/1998 | Barreras, Sr. et al. |
| 5,737,419 A | 4/1998 | Ganesan |
| 5,752,976 A | 5/1998 | Duffin et al. |
| 5,752,977 A | 5/1998 | Grevious et al. |
| 5,759,199 A | 6/1998 | Snell et al. |
| 5,764,699 A | 6/1998 | Needham et al. |
| 5,766,232 A | 6/1998 | Grevious et al. |
| 5,807,397 A | 9/1998 | Barreras |
| 5,833,603 A | 11/1998 | Kovacs et al. |
| 5,843,139 A | 12/1998 | Goedeke et al. |
| 5,861,019 A | 1/1999 | Sun et al. |
| 5,870,391 A | 2/1999 | Nago |
| 5,881,101 A | 3/1999 | Furman et al. |
| 5,887,022 A | 3/1999 | Lee |
| 5,895,485 A | 4/1999 | Loechel et al. |
| 5,898,397 A | 4/1999 | Murray |
| 5,904,708 A | 5/1999 | Goedeke |
| 5,919,210 A | 7/1999 | Lurie et al. |
| 5,940,384 A | 8/1999 | Carney et al. |
| 6,009,350 A | 12/1999 | Renken |
| 6,028,527 A | 2/2000 | Soenen et al. |
| 6,031,863 A | 2/2000 | Jusa et al. |
| 6,044,485 A | 3/2000 | Dent et al. |
| 6,083,248 A | 7/2000 | Thompson |
| 6,088,381 A | 7/2000 | Myers, Jr. |
| 6,093,146 A | 7/2000 | Filangeri |
| 6,115,583 A | 9/2000 | Brummer et al. |
| 6,115,634 A | 9/2000 | Donders et al. |
| 6,115,636 A | 9/2000 | Ryan |
| 6,128,528 A | 10/2000 | Erickson et al. |
| 6,130,905 A | 10/2000 | Wakayama |
| 6,155,208 A | 12/2000 | Schell et al. |
| 6,167,310 A | 12/2000 | Grevious |
| 6,167,312 A | 12/2000 | Goedeke |
| 6,169,925 B1 | 1/2001 | Villaseca et al. |
| 6,200,265 B1 | 3/2001 | Walsh et al. |
| 6,219,580 B1 | 4/2001 | Faltys et al. |
| 6,223,083 B1 | 4/2001 | Rosar |
| 6,240,317 B1 | 5/2001 | Villaseca et al. |
| 6,249,700 B1 | 6/2001 | Alt |
| 6,263,246 B1 | 7/2001 | Goedeke et al. |
| 6,275,737 B1 | 8/2001 | Mann |
| 6,309,350 B1 | 10/2001 | VanTassel et al. |
| 6,329,920 B1 | 12/2001 | Morrison et al. |
| 6,336,900 B1 | 1/2002 | Alleckson et al. |
| 6,336,903 B1 | 1/2002 | Bardy |
| 6,381,492 B1 | 4/2002 | Rockwell et al. |
| 6,385,318 B1 | 5/2002 | Oishi |
| 6,388,628 B1 | 5/2002 | Dettloff et al. |
| 6,416,471 B1 | 7/2002 | Kumar et al. |
| 6,424,867 B1 | 7/2002 | Snell et al. |
| 6,427,088 B1 | 7/2002 | Bowman, IV et al. |
| 6,434,429 B1 | 8/2002 | Kraus et al. |
| 6,443,891 B1 | 9/2002 | Grevious |
| 6,456,256 B1 | 9/2002 | Amundson et al. |
| 6,456,875 B1 | 9/2002 | Wilkinson et al. |
| 6,463,329 B1 | 10/2002 | Goedeke |
| 6,470,215 B1 | 10/2002 | Kraus et al. |
| 6,471,645 B1 | 10/2002 | Warkentin |
| 6,472,991 B1 | 10/2002 | Schulman et al. |
| 6,482,154 B1 | 11/2002 | Haubrich et al. |
| 6,490,487 B1 | 12/2002 | Kraus et al. |
| 6,505,072 B1 | 1/2003 | Linder et al. |
| 6,527,729 B1 | 3/2003 | Turcott |
| 6,531,982 B1 | 3/2003 | White et al. |
| 6,535,763 B1 | 3/2003 | Hiebert et al. |
| 6,535,766 B1 | 3/2003 | Thompson et al. |
| 6,562,000 B2 | 5/2003 | Thompson et al. |
| 6,562,001 B2 | 5/2003 | Lebel et al. |
| 6,564,104 B2 | 5/2003 | Nelson et al. |
| 6,564,105 B2 | 5/2003 | Starkweather et al. |
| 6,567,793 B1 | 5/2003 | Hicks et al. |
| 6,574,503 B2 | 6/2003 | Ferek-Petric |
| 6,574,509 B1 | 6/2003 | Kraus et al. |
| 6,574,510 B2 | 6/2003 | Von Arx et al. |
| 6,577,900 B1 | 6/2003 | Silvian |
| 6,577,901 B2 | 6/2003 | Thompson et al. |
| 6,582,365 B1 | 6/2003 | Hines et al. |
| 6,585,644 B2 | 7/2003 | Lebel et al. |
| 6,600,949 B1 | 7/2003 | Turcott |
| 6,600,952 B1 | 7/2003 | Snell et al. |
| 6,602,191 B2 | 8/2003 | Quy |
| 6,609,029 B1 | 8/2003 | Mann et al. |
| 6,614,406 B2 | 9/2003 | Amundson et al. |
| 6,622,043 B1 | 9/2003 | Kraus et al. |
| 6,622,050 B2 | 9/2003 | Thompson |
| 6,624,786 B2 | 9/2003 | Boyle |
| 6,631,296 B1 | 10/2003 | Parramon et al. |
| 6,648,821 B2 | 11/2003 | Lebel et al. |
| 6,659,948 B2 | 12/2003 | Lebel et al. |
| 6,662,048 B2 | 12/2003 | Balczewski et al. |
| 6,671,328 B1 | 12/2003 | Poon et al. |
| 6,675,045 B2 | 1/2004 | Mass et al. |
| 6,687,546 B2 | 2/2004 | Lebel et al. |
| 6,708,065 B2 | 3/2004 | Von Arx et al. |

(56) References Cited

U.S. PATENT DOCUMENTS

| | | |
|---|---|---|
| 6,716,165 B1 | 4/2004 | Flanders et al. |
| 6,741,886 B2 | 5/2004 | Yonce |
| 6,752,765 B1 | 6/2004 | Jensen et al. |
| 6,763,269 B2 | 7/2004 | Cox |
| 6,768,730 B1 | 7/2004 | Whitehill |
| 6,801,807 B2 | 10/2004 | Abrahamson |
| 6,804,559 B1 | 10/2004 | Kraus et al. |
| 6,809,701 B2 | 10/2004 | Amundson et al. |
| 6,844,854 B2 | 1/2005 | Johnson et al. |
| 6,868,288 B2 | 3/2005 | Thompson |
| 6,873,870 B2 | 3/2005 | Ferek-Petric |
| 6,889,081 B2 | 5/2005 | Hsu |
| 6,897,788 B2 | 5/2005 | Khair et al. |
| 6,907,291 B1 | 6/2005 | Snell et al. |
| 6,951,596 B2 | 10/2005 | Green et al. |
| 6,970,735 B2 | 11/2005 | Uber, III et al. |
| 6,978,181 B1 | 12/2005 | Snell |
| 6,985,088 B2 | 1/2006 | Goetz et al. |
| 6,985,773 B2 | 1/2006 | Von Arx et al. |
| 6,993,393 B2 | 1/2006 | Von Arx et al. |
| 7,013,178 B2 | 3/2006 | Reinke et al. |
| 7,027,872 B2 | 4/2006 | Thompson |
| 7,047,076 B1 | 5/2006 | Li et al. |
| 7,069,086 B2 | 6/2006 | Von Arx |
| 7,107,085 B2 | 9/2006 | Doi |
| 7,110,823 B2 | 9/2006 | Whitehurst et al. |
| 7,155,290 B2 | 12/2006 | Von et al. |
| 7,177,700 B1 | 2/2007 | Cox |
| 7,218,969 B2 | 5/2007 | Vallapureddy et al. |
| 7,228,182 B2 | 6/2007 | Healy et al. |
| 7,274,642 B2 | 9/2007 | Sako et al. |
| 7,280,872 B1 | 10/2007 | Mosesov et al. |
| 7,289,853 B1 | 10/2007 | Campbell et al. |
| 7,319,903 B2 | 1/2008 | Bange et al. |
| 7,324,012 B2 | 1/2008 | Mann et al. |
| 7,359,753 B2 | 4/2008 | Bange et al. |
| 7,406,349 B2 | 7/2008 | Seeberger et al. |
| 7,457,669 B2 | 11/2008 | Katoozi et al. |
| 7,475,245 B1 | 1/2009 | Healy et al. |
| 7,519,430 B2 | 4/2009 | Arx et al. |
| 7,539,489 B1 | 5/2009 | Alexander |
| 7,539,541 B2 | 5/2009 | Quiles et al. |
| 7,573,422 B2 | 8/2009 | Harvey et al. |
| 7,610,065 B2 | 10/2009 | Vallapureddy et al. |
| 7,623,922 B2 | 11/2009 | Bange et al. |
| 7,664,553 B2 * | 2/2010 | Roberts ............... 607/60 |
| 7,668,596 B2 | 2/2010 | Von Arx et al. |
| 7,729,776 B2 | 6/2010 | Von Arx et al. |
| 7,738,964 B2 | 6/2010 | Von Arx et al. |
| 7,787,953 B2 | 8/2010 | Vallapureddy et al. |
| 7,818,067 B2 | 10/2010 | Healy et al. |
| 7,860,574 B2 | 12/2010 | Von Arx et al. |
| 7,881,802 B2 | 2/2011 | Quiles et al. |
| 7,890,180 B2 | 2/2011 | Quiles |
| 7,903,043 B2 | 3/2011 | Rawat et al. |
| 8,019,434 B2 | 9/2011 | Quiles et al. |
| 8,024,043 B2 * | 9/2011 | Bange et al. ............ 607/32 |
| 8,041,432 B2 | 10/2011 | Von Arx et al. |
| 8,046,080 B2 | 10/2011 | Von Arx et al. |
| 8,055,350 B2 | 11/2011 | Roberts |
| 8,290,589 B2 | 10/2012 | Bange et al. |
| 8,326,424 B2 * | 12/2012 | Bange et al. ............ 607/32 |
| 2001/0001014 A1 | 5/2001 | Akins et al. |
| 2001/0012955 A1 | 8/2001 | Goedeke et al. |
| 2001/0019614 A1 | 9/2001 | Madoukh |
| 2001/0027331 A1 | 10/2001 | Thompson |
| 2001/0047125 A1 | 11/2001 | Quy |
| 2002/0013614 A1 | 1/2002 | Thompson |
| 2002/0019606 A1 | 2/2002 | Lebel et al. |
| 2002/0032661 A1 | 3/2002 | Schuba et al. |
| 2002/0046276 A1 | 4/2002 | Coffey et al. |
| 2002/0049480 A1 | 4/2002 | Lebel et al. |
| 2002/0062139 A1 | 5/2002 | Ding |
| 2002/0065509 A1 | 5/2002 | Lebel et al. |
| 2002/0065539 A1 | 5/2002 | Von Arx et al. |
| 2002/0065540 A1 | 5/2002 | Lebel et al. |
| 2002/0109621 A1 | 8/2002 | Khair et al. |
| 2002/0115912 A1 | 8/2002 | Muraki et al. |
| 2002/0120838 A1 | 8/2002 | Abdulkader |
| 2002/0123672 A1 | 9/2002 | Christophersom et al. |
| 2002/0143372 A1 | 10/2002 | Snell et al. |
| 2002/0147388 A1 | 10/2002 | Mass et al. |
| 2002/0159545 A1 | 10/2002 | Ramesh et al. |
| 2002/0173830 A1 | 11/2002 | Starkweather et al. |
| 2002/0183806 A1 | 12/2002 | Abrahamson et al. |
| 2003/0009204 A1 | 1/2003 | Amundson et al. |
| 2003/0018369 A1 | 1/2003 | Thompson et al. |
| 2003/0028902 A1 | 2/2003 | Cubley et al. |
| 2003/0041866 A1 | 3/2003 | Linberg et al. |
| 2003/0050535 A1 | 3/2003 | Bowman, IV et al. |
| 2003/0065919 A1 | 4/2003 | Albert et al. |
| 2003/0074036 A1 | 4/2003 | Prutchi et al. |
| 2003/0083719 A1 | 5/2003 | Shankar et al. |
| 2003/0097157 A1 | 5/2003 | Wohlgemuth et al. |
| 2003/0107487 A1 | 6/2003 | Korman et al. |
| 2003/0114891 A1 | 6/2003 | Hiebert et al. |
| 2003/0114897 A1 | 6/2003 | Von Arx et al. |
| 2003/0114898 A1 | 6/2003 | Von Arx et al. |
| 2003/0135246 A1 | 7/2003 | Mass et al. |
| 2003/0146835 A1 | 8/2003 | Carter |
| 2003/0149459 A1 | 8/2003 | Von Arx et al. |
| 2003/0159048 A1 | 8/2003 | Matsumoto et al. |
| 2003/0174069 A1 | 9/2003 | Goetz et al. |
| 2003/0187484 A1 | 10/2003 | Davis et al. |
| 2003/0216793 A1 | 11/2003 | Karlsson et al. |
| 2003/0220673 A1 | 11/2003 | Snell |
| 2004/0009815 A1 | 1/2004 | Zotto et al. |
| 2004/0030260 A1 | 2/2004 | Von Arx |
| 2004/0047434 A1 | 3/2004 | Waltho |
| 2004/0102815 A1 | 5/2004 | Balczewski et al. |
| 2004/0106967 A1 | 6/2004 | Von Arx et al. |
| 2004/0122489 A1 | 6/2004 | Mazar et al. |
| 2004/0127959 A1 | 7/2004 | Amundson et al. |
| 2004/0167587 A1 | 8/2004 | Thompson |
| 2004/0168071 A1 | 8/2004 | Silverbrook |
| 2004/0176811 A1 | 9/2004 | Von Arx et al. |
| 2004/0176822 A1 | 9/2004 | Thompson et al. |
| 2004/0215280 A1 | 10/2004 | Dublin et al. |
| 2004/0236382 A1 | 11/2004 | Dinsmoor et al. |
| 2004/0247047 A1 | 12/2004 | Dennis et al. |
| 2004/0260363 A1 | 12/2004 | Arx et al. |
| 2004/0263273 A1 | 12/2004 | Ahmed |
| 2005/0134520 A1 | 6/2005 | Rawat et al. |
| 2005/0203582 A1 | 9/2005 | Healy et al. |
| 2005/0204134 A1 | 9/2005 | Von Arx et al. |
| 2005/0222933 A1 | 10/2005 | Wesby |
| 2005/0240245 A1 | 10/2005 | Bange et al. |
| 2005/0245992 A1 | 11/2005 | Persen et al. |
| 2005/0261934 A1 | 11/2005 | Thompson |
| 2005/0283208 A1 | 12/2005 | Von Arx et al. |
| 2005/0283209 A1 | 12/2005 | Katoozi et al. |
| 2005/0288738 A1 | 12/2005 | Bange et al. |
| 2006/0025834 A1 | 2/2006 | Von Arx et al. |
| 2006/0029100 A1 | 2/2006 | Dove |
| 2006/0030901 A1 | 2/2006 | Quiles et al. |
| 2006/0030902 A1 | 2/2006 | Quiles et al. |
| 2006/0030903 A1 | 2/2006 | Seeberger et al. |
| 2006/0030904 A1 | 2/2006 | Quiles |
| 2006/0071756 A1 | 4/2006 | Steeves |
| 2006/0116744 A1 | 6/2006 | Von Arx et al. |
| 2006/0161222 A1 | 7/2006 | Haubrich et al. |
| 2006/0161223 A1 | 7/2006 | Vallapureddy et al. |
| 2006/0194615 A1 | 8/2006 | Vallapureddy et al. |
| 2006/0195161 A1 | 8/2006 | Li |
| 2006/0195162 A1 | 8/2006 | Arx et al. |
| 2006/0247736 A1 | 11/2006 | Roberts |
| 2007/0049983 A1 | 3/2007 | Freeberg |
| 2007/0100396 A1 | 5/2007 | Freeberg |
| 2007/0118188 A1 | 5/2007 | Von Arx et al. |
| 2007/0135216 A1 | 6/2007 | Martinek et al. |
| 2007/0169181 A1 | 7/2007 | Roskind |
| 2007/0185550 A1 | 8/2007 | Vallapureddy et al. |
| 2007/0260293 A1 | 11/2007 | Carpenter et al. |
| 2007/0282398 A1 | 12/2007 | Healy et al. |

(56) References Cited

U.S. PATENT DOCUMENTS

| | | |
|---|---|---|
| 2008/0015655 A1 | 1/2008 | Bange et al. |
| 2008/0015656 A1 | 1/2008 | Bange et al. |
| 2008/0046745 A1 | 2/2008 | Buch et al. |
| 2008/0055070 A1 | 3/2008 | Bange et al. |
| 2008/0114412 A1 | 5/2008 | Bange et al. |
| 2008/0215121 A1 | 9/2008 | Bange et al. |
| 2008/0262573 A1 | 10/2008 | Seeberger et al. |
| 2008/0288024 A1 | 11/2008 | Abrahamson |
| 2009/0216298 A1 | 8/2009 | Quiles et al. |
| 2010/0045480 A1 | 2/2010 | Vallapureddy et al. |
| 2010/0106224 A1 | 4/2010 | Von Arx et al. |
| 2010/0114233 A1 | 5/2010 | Von Arx et al. |
| 2010/0121414 A1 | 5/2010 | Roberts |
| 2010/0152816 A1 | 6/2010 | Von Arx et al. |
| 2011/0066211 A1 | 3/2011 | Von Arx et al. |
| 2011/0098788 A1 | 4/2011 | Quiles |
| 2011/0134013 A1 | 6/2011 | Rawat et al. |
| 2011/0313491 A1 | 12/2011 | Bange et al. |

FOREIGN PATENT DOCUMENTS

| | | |
|---|---|---|
| EP | 0607638 A2 | 7/1994 |
| EP | 1050265 | 11/2000 |
| EP | 1062985 A2 | 12/2000 |
| EP | 1308184 A2 | 5/2003 |
| EP | 1495783 A1 | 1/2005 |
| EP | 1732645 B1 | 6/2012 |
| JP | 08511702 | 12/1996 |
| JP | 2001274901 A | 10/2001 |
| JP | 2002132962 A | 5/2002 |
| JP | 2003022008 A | 1/2003 |
| JP | 2004094544 A | 3/2004 |
| WO | WO-9500202 A1 | 1/1995 |
| WO | WO-9819400 A1 | 5/1998 |
| WO | WO-9912302 A1 | 3/1999 |
| WO | WO-03053515 A1 | 7/2003 |
| WO | WO-03092240 A1 | 11/2003 |
| WO | WO-2005000397 A1 | 1/2005 |
| WO | WO-2005091546 A2 | 9/2005 |
| WO | WO-2005091546 A3 | 9/2005 |
| WO | WO-2005099816 A1 | 10/2005 |
| WO | WO-2005099817 A1 | 10/2005 |
| WO | WO-2006020546 A1 | 2/2006 |
| WO | WO-2006020549 A1 | 2/2006 |
| WO | WO-2006116004 A1 | 11/2006 |
| WO | WO-2008027655 A1 | 3/2008 |

OTHER PUBLICATIONS

"U.S. Appl. No. 09/921,653, Notice of Allowance mailed May 7, 2002", 6 pgs.
"U.S. Appl. No. 10/025,183, Appeal Brief filed Dec. 29, 2005", 27 pgs.
"U.S. Appl. No. 10/025,183, Final Office Action mailed Jan. 13, 2005", 7 pgs.
"U.S. Appl. No. 10/025,183, Final Office Action mailed May 25, 2005", 9 pgs.
"U.S. Appl. No. 10/025,183, Final Office Action mailed Jul. 31, 2006", 7 pgs.
"U.S. Appl. No. 10/025,183, Final Office Action mailed Aug. 3, 2004", 7 pgs.
"U.S. Appl. No. 10/025,183, Non-Final Office Action mailed Feb. 15, 2006", 5 pgs.
"U.S. Appl. No. 10/025,183, Non-Final Office Action mailed Feb. 19, 2009", 5 pgs.
"U.S. Appl. No. 10/025,183, Non-Final Office Action mailed Mar. 4, 2004", 5 pgs.
"U.S. Appl. No. 10/025,183, Non-Final Office Action mailed Mar. 26, 2007", 4 pgs.
"U.S. Appl. No. 10/025,183, Non-Final Office Action mailed Dec. 10, 2007", 4 pgs.
"U.S. Appl. No. 10/025,183, Notice of Allowance mailed Sep. 14, 2007", 4 pgs.
"U.S. Appl. No. 10/025,183, Notice of Allowance mailed Sep. 18, 2008", 7 pgs.
"U.S. Appl. No. 10/025,183, Notice of Allowance mailed Sep. 28, 2009", 5 pgs.
"U.S. Appl. No. 10/025,183, Response filed Jan. 31, 2007 to Final Office Action mailed Jul. 31, 2006", 11 pgs.
"U.S. Appl. No. 10/025,183, Response filed Apr. 13, 2005 to Final Office Action mailed Jan. 13, 2005", 11 pgs.
"U.S. Appl. No. 10/025,183, Response filed May 12, 2008 to Non-Final Office Action mailed Dec. 10, 2007", 10 pgs.
"U.S. Appl. No. 10/025,183, Response filed May 15, 2006 to Non-Final Office Action mailed Feb. 15, 2006", 11 pgs.
"U.S. Appl. No. 10/025,183, Response filed Jun. 24, 2004 to Non-Final Office Action mailed Mar. 4, 2004", 11 pgs.
"U.S. Appl. No. 10/025,183, Response filed Jun. 12, 2009 to Non Final Office Action mailed Feb. 19, 2009", 10 pgs.
"U.S. Appl. No. 10/025,183, Response filed Jun. 26, 2007 to Non-Final Office Action mailed Mar. 26, 2007", 14 pgs.
"U.S. Appl. No. 10/025,183, Response filed Dec. 3, 2004 to Final Office Action mailed Aug. 3, 2004", 11 pgs.
"U.S. Appl. No. 10/025,223, Communication filed Nov. 16, 2004 to Final Office Action mailed Aug. 16, 2004", 1 pg.
"U.S. Appl. No. 10/025,223, Final Office Action mailed Aug. 16, 2004", 9 pgs.
"U.S. Appl. No. 10/025,223, Final Office Action mailed Aug. 16, 2004", 7 pgs.
"U.S. Appl. No. 10/025,223, Final Office Action mailed Sep. 10, 2004", 7 pgs.
"U.S. Appl. No. 10/025,223, Non Final Office Action mailed Mar. 1, 2005", 6 pgs.
"U.S. Appl. No. 10/025,223, Non Final Office Action mailed Mar. 19, 2004", 4 pgs.
"U.S. Appl. No. 10/025,223, Non-Final Office Action mailed Mar. 19, 2004", 4 pgs.
"U.S. Appl. No. 10/025,223, Non-Final Office Action mailed Mar. 1, 2005", 6 pgs.
"U.S. Appl. No. 10/025,223, Notice of Allowance mailed Aug. 10, 2005", 4 pgs.
"U.S. Appl. No. 10/025,223, Response filed Jan. 10, 2005 to Final Office Action mailed Sep. 10, 2004", 10 pgs.
"U.S. Appl. No. 10/025,223, Response filed Jun. 21, 2004 to Non Final Office Action mailed Mar. 19, 2004", 9 pgs.
"U.S. Appl. No. 10/025,223, Response filed Jun. 30, 2005 to Non Final Office Action mailed Mar. 1, 2005", 10 pgs.
"U.S. Appl. No. 10/071,255, Non Final Office Action mailed Jan. 7, 2005", 6 pgs.
"U.S. Appl. No. 10/071,255, Notice of allowance mailed Jun. 15, 2005", 4 pgs.
"U.S. Appl. No. 10/071,255, Preliminary Amendment filed Oct. 5, 2005", 12 pgs.
"U.S. Appl. No. 10/071,255, Response Oct. 20, 2004 to Restriction Requirement mailed Sep. 28, 2004", 10 pgs.
"U.S. Appl. No. 10/071,255, Response filed Apr. 7, 2005 non-final office action mailed Jan. 7, 2005", 12 pgs.
"U.S. Appl. No. 10/071,255, Restriction Requirement mailed Sep. 28, 2004", 5 pgs.
"U.S. Appl. No. 10/252,494, Non Final Office Action mailed Jan. 30, 2003", 4 pgs.
"U.S. Appl. No. 10/252,494, Notice of Allowance mailed Mar. 25, 2003", 5 pgs.
"U.S. Appl. No. 10/252,494, Response filed Mar. 5, 2003 to Non Final Office Action mailed Jan. 30, 2003", 6 pgs.
"U.S. Appl. No. 10/269,905, Non Final Office Action mailed Jul. 27, 2005", 15 pgs.
"U.S. Appl. No. 10/269,905, Notice of Allowance mailed Jan. 20, 2006", 11 pgs.
"U.S. Appl. No. 10/269,905, Response filed Nov. 28, 2005 to Non Final Office Action mailed Jul. 27, 2005", 13 pgs.
"U.S. Appl. No. 10/634,233, Notice of Allowance mailed Jun. 16, 2004", 6 pgs.
"U.S. Appl. No. 10/744,943, Final Office Action mailed Feb. 21, 2008.", 15 pgs.

(56) References Cited

OTHER PUBLICATIONS

"U.S. Appl. No. 10/744,943, Response filed Oct. 22, 2007 to Non-Final Office Action mailed Apr. 20, 2007", 9 pgs.

"U.S. Appl. No. 10/870,324, Advisory Action mailed Mar. 21, 2008", 3 pgs.

"U.S. Appl. No. 10/870,324, Examiner Interview Summary mailed Feb. 13, 2008", 4 pgs.

"U.S. Appl. No. 10/870,324, Examiner Interview Summary mailed Sep. 28, 2007", 3 pgs.

"U.S. Appl. No. 10/870,324, Examiner Interview Summary mailed Oct. 25, 2007", 3 pgs.

"U.S. Appl. No. 10/870,324, Final Office Action mailed Jan. 8, 2008", 8 pgs.

"U.S. Appl. No. 10/870,324, Non Final Office Action mailed Jun. 27, 2007", 6 pgs.

"U.S. Appl. No. 10/870,324, Non-Final Office Action mailed May 14, 2008", 8 pgs.

"U.S. Appl. No. 10/870,324, Notice of Allowance mailed Dec. 1, 2008", 7 pgs.

"U.S. Appl. No. 10/870,324, Response filed Feb. 8, 2008 to Final Office Action mailed Jan. 8, 2008", 20 pgs.

"U.S. Appl. No. 10/870,324, Response filed Aug. 14, 2008 to Non-Final Office Action mailed May 14, 2008", 22 pgs.

"U.S. Appl. No. 10/870,324, Response filed Oct. 29, 2007 to Non Final Office Action mailed Jun. 27, 2007", 21 pgs.

"U.S. Appl. No. 10/870,328, Non Final Office Action mailed Aug. 16, 2007", 12 pgs.

"U.S. Appl. No. 10/870,328, Notice of Allowance mailed Jul. 24, 2008", 10 pgs.

"U.S. Appl. No. 10/870,328, Response filed Nov. 16, 2007 to Non-Final Office Action mailed Aug. 16, 2007", 17 pgs.

"U.S. Appl. No. 10/914,496, Final Office Action mailed May 23, 2007", 11 pgs.

"U.S. Appl. No. 10/914,496, Final Office Action mailed Sep. 22, 2008", 12 pgs.

"U.S. Appl. No. 10/914,496, Non Final Office Action mailed Dec. 5, 2006", 9 pgs.

"U.S. Appl. No. 10/914,496, Non-Final Office Action mailed Mar. 18, 2008", 9 pgs.

"U.S. Appl. No. 10/914,496, Notice of Allowance mailed Jan. 16, 2009", 4 pgs.

"U.S. Appl. No. 10/914,496, Response filed Mar. 5, 2007 to Non Final office Action mailed Dec. 5, 2006", 13 pgs.

"U.S. Appl. No. 10/914,496, Response filed Jun. 18, 2008 to Non-Final Office Action mailed Mar. 18, 2008", 10 pgs.

"U.S. Appl. No. 10/914,496, Response filed Aug. 22, 2007 to Final Office Action mailed May 23, 2007", 12 pgs.

"U.S. Appl. No. 10/914,496, Response filed Nov. 24, 2008 to Final Office Action mailed Sep. 22, 2008", 9 pgs.

"U.S. Appl. No. 10/914,496, Response filed Dec. 12, 2007 to Restriction Requirement mailed Nov. 13, 2007", 7 pgs.

"U.S. Appl. No. 10/914,496, Restriction Requirement mailed Nov. 13, 2007", 5 pgs.

"U.S. Appl. No. 10/914,499, Advisory Action mailed Aug. 4, 2009", 5 pgs.

"U.S. Appl. No. 10/914,499, Final Office Action mailed Jan. 24, 2008", 10 pgs.

"U.S. Appl. No. 10/914,499, Final Office Action mailed May 12, 2009", 10 pgs.

"U.S. Appl. No. 10/914,499, Non Final Office Action mailed May 29, 2007", 11 pgs.

"U.S. Appl. No. 10/914,499, Non-Final Office Action mailed Feb. 3, 2010", 11 pgs.

"U.S. Appl. No. 10/914,499, Non-Final Office Action mailed Apr. 24, 2008", 5 pgs.

"U.S. Appl. No. 10/914,499, Non-Final Office Action mailed Nov. 5, 2008", 12 pgs.

"U.S. Appl. No. 10/914,499, Notice of Allowance mailed Sep. 29, 2010", 4 pgs.

"U.S. Appl. No. 10/914,499, Response filed Feb. 5, 2009 to Non-Final Office Action mailed Nov. 5, 2008", 12 pgs.

"U.S. Appl. No. 10/914,499, Response filed Apr. 14, 2008 to Final Office Action mailed Jan. 24, 2008", 11 pgs.

"U.S. Appl. No. 10/914,499, Response filed May 3, 2010 to Non-Final Office Action mailed Feb. 3, 2010", 12 pgs.

"U.S. Appl. No. 10/914,499, Response filed Jun. 30, 2008 to Non-Final Office Action mailed Apr. 24, 2008", 10 pgs.

"U.S. Appl. No. 10/914,499, Response filed Jul. 13, 2009 to Final Office Action mailed May 12, 2009", 10 pgs.

"U.S. Appl. No. 10/914,499, Response filed Aug. 31, 2010 to Final Office Action mailed Jul. 20, 2010", 10 pgs.

"U.S. Appl. No. 10/914,499, Response filed Oct. 23, 2007 to Non-Final Office Action mailed May 29, 2007", 11 pgs.

"U.S. Appl. No. 10/914,499, Response filed Nov. 10, 2009 to Advisory Action mailed Aug. 4, 2009", 12 pgs.

"U.S. Appl. No. 10/914,638, Final Office Action mailed Apr. 17, 2007", 10 pgs.

"U.S. Appl. No. 10/914,638, Non Final Office Action mailed Oct. 18, 2006", 9 pgs.

"U.S. Appl. No. 10/914,638, Notice of Allowance mailed Mar. 21, 2008", 4 pgs.

"U.S. Appl. No. 10/914,638, Notice of Allowance mailed Oct. 22, 2007", 4 pgs.

"U.S. Appl. No. 10/914,638, Response filed Jan. 18, 2007 to Non Final Office Action mailed Oct. 18, 2006", 16 pgs.

"U.S. Appl. No. 10/914,638, Response filed Aug. 17, 2007 to Final Office Action mailed Apr. 17, 2007", 8 pgs.

"U.S. Appl. No. 11/039,200, Non Final Office Action mailed Aug. 3, 2006", 10 pgs.

"U.S. Appl. No. 11/039,200, Notice of Allowance mailed Dec. 15, 2006", 4 pgs.

"U.S. Appl. No. 11/039,200, Response filed Nov. 2, 2006 to Non Final Office Action mailed Aug. 3, 2006", 9 pgs.

"U.S. Appl. No. 11/068,478, Final Office Action mailed Jun. 2, 2008", 17 pgs.

"U.S. Appl. No. 11/068,478, Non Final Office Action mailed Jan. 2, 2009", 11 pgs.

"U.S. Appl. No. 11/068,478, Non-Final Office Action mailed Dec. 17, 2007", 14 pgs.

"U.S. Appl. No. 11/068,478, Notice of Allowance mailed Jun. 9, 2009", 7 pgs.

"U.S. Appl. No. 11/068,478, Response filed Mar. 17, 2008 to Non Final Office Action mailed Dec. 17, 2007", 19 pgs.

"U.S. Appl. No. 11/068,478, Response filed Mar. 30, 2009 to Non Final Office Action mailed Jan. 2, 2009", 20 pgs.

"U.S. Appl. No. 11/068,478, Response filed Aug. 4, 2008 to Final Office Action mailed Jun. 2, 2008", 19 pgs.

"U.S. Appl. No. 11/101,142, Non-Final Office Action mailed Jun. 20, 2007", 8 pgs.

"U.S. Appl. No. 11/101,142, Notice of Allowance mailed Nov. 27, 2007", 6 pgs.

"U.S. Appl. No. 11/101,142, Response filed Jun. 4, 2007 to Restriction Requirement Response mailed May 3, 2007", 7 pgs.

"U.S. Appl. No. 11/101,142, Response filed Sep. 20, 2007 to Non-Final Office Action mailed Jun. 20, 2007", 7 pgs.

"U.S. Appl. No. 11/101,142, Restriction Requirement mailed May 3, 2007", 5 pgs.

"U.S. Appl. No. 11/101,196, Non Final Office Action mailed Mar. 29, 2007", 8 pgs.

"U.S. Appl. No. 11/101,196, Notice of Allowance mailed Aug. 27, 2007", 5 pgs.

"U.S. Appl. No. 11/101,196, Response filed Jun. 29, 2007 to Non Final Office Action mailed Mar. 29, 2007", 8 pgs.

"U.S. Appl. No. 11/116,108, Advisory Action mailed Jan. 29, 2009", 3 pgs.

"U.S. Appl. No. 11/116,108, Final Office Action mailed Oct. 10, 2008", 7 pgs.

"U.S. Appl. No. 11/116,108, Non-Final Office Action mailed Mar. 20, 2008", 11 pgs.

"U.S. Appl. No. 11/116,108, Non-Final Office Action mailed Apr. 23, 2009", 7 pgs.

(56) References Cited

OTHER PUBLICATIONS

"U.S. Appl. No. 11/116,108, Notice of Allowance mailed Sep. 29, 2009", 8 pgs.
"U.S. Appl. No. 11/116,108, Response filed Jun. 20, 2008 to Non-Final Office Action mailed Mar. 20, 2008", 9 pgs.
"U.S. Appl. No. 11/116,108, Response filed Jul. 23, 2009 to Non Final Office Action mailed Apr. 23, 2009", 7 pgs.
"U.S. Appl. No. 11/116,108, Response filed Dec. 10, 2008 to Final Office Action mailed Oct. 10, 2008", 6 pgs.
"U.S. Appl. No. 11/244,273, Non-Final Office Action mailed Nov. 28, 2008", 7 pgs.
"U.S. Appl. No. 11/244,273, Notice of Allowance mailed Oct. 5, 2009", 7 pgs.
"U.S. Appl. No. 11/244,273, Response filed Mar. 2, 2009 to Non-Final Office Action mailed Nov. 28, 2008", 13 pgs.
"U.S. Appl. No. 11/244,273, Response filed Aug. 12, 2009 to Ex Parte Quayle mailed Jun. 12, 2009", 4 pgs.
"U.S. Appl. No. 11/244,273, Response filed Oct. 22, 2008 to Restriction Requirement mailed Jul. 22, 2008", 13 pgs.
"U.S. Appl. No. 11/244,273, Restriction Requirement mailed Jul. 22, 2008", 10 pgs.
"U.S. Appl. No. 11/325,564, Examiner Interview Summary mailed Jun. 24, 2009", 2 pgs.
"U.S. Appl. No. 11/325,584, Final Office Action mailed Oct. 24, 2008", 5 pgs.
"U.S. Appl. No. 11/325,584, Non-Final Office Action mailed Mar. 24, 2009", 5 pgs.
"U.S. Appl. No. 11/325,584, Non-Final Office Action mailed Apr. 10, 2008", 6 pgs.
"U.S. Appl. No. 11/325,584, Notice of Allowance mailed Mar. 23, 2010", 4 pgs.
"U.S. Appl. No. 11/325,584, Notice of Allowance mailed Oct. 21, 2009", 5 pgs.
"U.S. Appl. No. 11/325,584, Response filed Jan. 22, 2009 to Final Office Action mailed Oct. 24, 2008", 6 pgs.
"U.S. Appl. No. 11/325,584, Response filed Jun. 24, 2009 to Non-Final Office Action mailed Mar. 24, 2009", 9 pgs.
"U.S. Appl. No. 11/325,584, Response filed Jul. 10, 2008 to Non Final Office Action mailed Apr. 10, 2008", 9 pgs.
"U.S. Appl. No. 11/381,493, Appeal Brief filed Nov. 16, 2009", 19 pgs.
"U.S. Appl. No. 11/381,493, Examiners Answer mailed Mar. 25, 2010", 20 pgs.
"U.S. Appl. No. 11/381,493, Final Office Action mailed Jan. 8, 2009", 12 pgs.
"U.S. Appl. No. 11/381,493, Final Office Action mailed Apr. 16, 2009", 14 pgs.
"U.S. Appl. No. 11/381,493, Non-Final Office Action mailed Jun. 23, 2008", 13 pgs.
"U.S. Appl. No. 11/381,493, Reply Brief filed Apr. 29, 2010", 6 pgs.
"U.S. Appl. No. 11/381,493, Response filed Mar. 9, 2009 to Final Office Action mailed Jan. 8, 2009", 13 pgs.
"U.S. Appl. No. 11/381,493, Response filed Apr. 28, 2008 to Restriction Requirement mailed Mar. 26, 2008", 9 pgs.
"U.S. Appl. No. 11/381,493, Response filed Jun. 9, 2009 to Final Office Action mailed Apr. 16, 2009", 13 pgs.
"U.S. Appl. No. 11/381,493, Response filed Sep. 22, 2008 to Non-Final Office Action mailed Jun. 23, 2008", 15 pgs.
"U.S. Appl. No. 11/381,493, Restriction Requirement mailed Mar. 26, 2008", 7 pgs.
"U.S. Appl. No. 11/640,552, Response filed Auag. 11, 2009 to Non Final Office Action mailed May 11, 2009", 10 pgs.
"U.S. Appl. No. 11/733,339, Examiner Interview Summary mailed Aug. 13, 2009", 2 pgs.
"U.S. Appl. No. 11/733,339, Non-Final Office Action mailed Apr. 30, 2009", 10 pgs.
"U.S. Appl. No. 11/733,339, Non-Final Office Action mailed Sep. 9, 2009", 9 pgs.
"U.S. Appl. No. 11/733,339, Notice of Allowance mailed Feb. 25, 2010", 6 pgs.
"U.S. Appl. No. 11/733,339, Notice of Allowance mailed Apr. 21, 2010", 6 pgs.
"U.S. Appl. No. 11/733,339, Response filed Dec. 4, 2009 to Non Final Office Action mailed Sep. 9, 2009", 11 pgs.
"U.S. Appl. No. 12/004,892, Final Office Action mailed Sep. 14, 2011", 8 pgs.
"U.S. Appl. No. 12/004,892, Response filed Jan. 4, 2012 to Final Office Action mailed Sep. 14, 2011", 11 pgs.
"U.S. Appl. No. 12/102,480, Final Office Action mailed Jan. 18, 2011", 6 pgs.
"U.S. Appl. No. 12/102,480, Non-Final Office Action mailed Aug. 18, 2010", 9 pgs.
"U.S. Appl. No. 12/102,480, Notice of Allowance mailed May 19, 2011", 8 pgs.
"U.S. Appl. No. 12/102,480, Response filed Apr. 18, 2011 to Final Office Action mailed Jan. 18, 2011", 9 pgs.
"U.S. Appl. No. 12/102,480, Response filed Nov. 18, 2010 to Non Final Office Action mailed Aug. 18, 2010", 13 pgs.
"U.S. Appl. No. 12/435,928, Non-Final Office Action mailed Oct. 22, 2010", 14 pgs.
"U.S. Appl. No. 12/435,928, Notice of Allowance mailed May 4, 2011", 9 pgs.
"U.S. Appl. No. 12/435,928, Response filed Jan. 21, 2011 to Non Final Office Action mailed Oct. 22, 2010", 13 pgs.
"U.S. Appl. No. 12/648,687, Notice of Allowance mailed Aug. 17, 2010", 7 pgs.
"U.S. Appl. No. 12/684,303, Non Final Office Action mailed Apr. 5, 2011", 5 pgs.
"U.S. Appl. No. 12/691,364, Advisory Action mailed Mar. 30, 2011", 3 pgs.
"U.S. Appl. No. 12/691,364, Final Office Action mailed Dec. 28, 2010", 8 pgs.
"U.S. Appl. No. 12/691,364, Non-Final Office Action mailed Jul. 20, 2010", 7 pgs.
"U.S. Appl. No. 12/691,364, Notice of Allowance mailed Sep. 13, 2011", 7 pgs.
"U.S. Appl. No. 12/691,364, Response filed Feb. 17, 2011 to Final Office Action mailed Dec. 28, 2010", 9 pgs.
"U.S. Appl. No. 12/691,364, Response filed Oct. 18, 2010 to Non-Final Office Action mailed Jul. 20, 2010", 11 pgs.
"U.S. Appl. No. 12/713,669, Non-Final Office Action mailed Mar. 2, 2011", 5 pgs.
"U.S. Appl. No. 12/713,669, Notice of Allowance mailed Jun. 24, 2011", 5 pgs.
"U.S. Appl. No. 12/713,669, Response filed May 16, 2011 to Non-Final Office Action mailed Mar. 2, 2011", 8 pgs.
"U.S. Appl. No. 13/218,672, Non Final Office Action mailed Mar. 15, 2012", 6 pgs.
"U.S. Appl. No. 13/218,672, Notice of Allowance mailed Aug. 6, 2012", 7 pgs.
"U.S. Appl. No. 13/218,672, Response filed Jun. 14, 2012 to Non Final Office Action mailed Mar. 15, 2012", 9 pgs.
"European Application Serial No. 02799254.4, Office Action mailed Sep. 23, 2009", 4 pgs.
"European Application Serial No. 05732873.4, Communication dated Feb. 13, 2007", 3 pgs.
"European Application Serial No. 05732873.4, Communication dated Nov. 15, 2006", 2 pgs.
"European Application Serial No. 05732873.4, Office Action mailed Mar. 23, 2010", 2 pgs.
"European Application Serial No. 05732873.4, Response filed Aug. 10, 2007 to Communication dated Feb. 13, 2007", 13 pgs.
"European Application Serial No. 05732873.4, Response filed Oct. 1, 2010 to Office Action mailed Mar. 23, 2010", 11 pgs.
"European Application Serial No. 05737578.4, Communication dated Feb. 13, 2007", 3 pgs.
"European Application Serial No. 05737578.4, European Office Action mailed Jul. 13, 2010", 4 pgs.
"European Application Serial No. 05737578.4, Office Action Response Filed Nov. 22, 2010", 12 pgs.
"European Application Serial No. 05737578.4, Response filed Aug. 10, 2007 to Communication dated Feb. 13, 2007", 15 pgs.

(56) References Cited

OTHER PUBLICATIONS

"European Application Serial No. 05783799.9, Communication pursuant to Article 94(3) EPC mailed Jun. 16, 2009", 3 pgs.
"European Application Serial No. 05783799.9, Office Action mailed Oct. 25, 2010", 3 pgs.
"European Application Serial No. 05783799.9, Response filed Mar. 3, 2011 to Office Action mailed Oct. 25, 2010", 12 pgs.
"European Application Serial No. 05783799.9, Response filed Oct. 23, 2009 to Communication mailed Jun. 16, 2009", 9 pgs.
"European Application Serial No. 05783882.3, Communication pursuant to Article 94(3) EPC mailed Jun. 16, 2009", 3 pgs.
"European Application Serial No. 06750873.9, Office Action mailed Apr. 14, 10", 5 pgs.
"European Application Serial No. 06750873.9, Office Action mailed May 7, 2009", 2 pgs.
"European Application Serial No. 06750873.9, Office Action Response Filed Oct. 22, 2010", 13 pgs.
"European Application Serial No. 06750873.9, Response filed Sep. 16, 2009 to Communication mailed May 7, 2009", 7 pgs.
"International Application No. PCT/US2002/040488, International Search Report mailed May 9, 2003", 7 pgs.
"International Application No. PCT/US2003/003748, International Search Report mailed Oct. 20, 2003", 5 pgs.
"International Application No. PCT/US2005/011606, International Search Report and Written Opinion mailed Jul. 26, 2005", 12 pgs.
"International Application No. PCT/US2005/011639, International Search Report and Written Opinion mailed Aug. 26, 2005", 12 pgs.
"International Application No. PCT/US2005/028052, International Preliminary Report on Patentability mailed Feb. 22, 2007", 8 pgs.
"International Application No. PCT/US2005/028052, International Search Report and Written Opinion mailed Nov. 29, 2005", 12 pgs.
"International Application No. PCT/US2005/028059, International Preliminary Report on Patentability mailed Feb. 13, 2007", 9 pgs.
"International Application No. PCT/US2005/028059, International Search Report and Written Opinion mailed Jan. 12, 2005", 13 pgs.
"International Application No. PCT/US2005/028059, International Search Report and Written Opinion mailed Dec. 1, 2005", 13 pgs.
"International Application No. PCT/US2006/014957, International Search Report and Written Opinion mailed Sep. 29, 2006", 16 pgs.
"International Application No. PCT/US2007/069424, International Search Report mailed Dec. 27, 2007", 4 pgs.
"International Application No. PCT/US2007/069424, Written Opinion mailed Dec. 27, 2007", 9 pgs.
"International Application No. PCT/US2007/069426, International Search Report mailed Dec. 27, 2007", 4 pgs.
"International Application No. PCT/US2007/069426, Written Opinion mailed Dec. 27, 2007", 8 pgs.
"International Application No. PCT/US2007/072827, International Search Report mailed Dec. 10, 2007", 4 pgs.
"International Application No. PCT/US2007/072827, Written Opinion mailed Dec. 10, 2007", 6 pgs.
"Japanese Application Serial No. 2007-507458, Office Action mailed Aug. 31, 2010", (w/ English Translation), 4 pgs.
"Japanese Application Serial No. 2007-507458, Office Action Response Filed: Nov. 26, 2010", (w/ English Translation of amended claims), 6 pgs.
"Japanese Application Serial No. 2007-507465, Notice of Allowance mailed Feb. 14, 2011", 3 pgs.
"Japanese Application Serial No. 2007-507465, Office Action mailed Sep. 1, 2010", 4 pgs.
"Japanese Application Serial No. 2007-507465, Office Action Response Filed Nov. 24, 2010", 10 pgs.
"Japanese Application Serial No. 2007-525697, Office Action mailed Apr. 19, 2011", (w/ English Translation), 7 pgs.
"Part III—Department of Health and Human Services, Office of the Secretary—45 CFR Part 142—Security and Electronic Signature Standards; Proposed Rule", Federal Register, 63(155), (Aug. 12, 1998), 43241-43280.

"Public Law 104-191 [H.R. 3103]—Health Insurance Portability and Accountability Act of 1996", United States Public Laws—104th Congress—2nd Session, (Aug. 21, 1996), 78 pgs.
Adams, J. T, "An introduction to IEEE STD 802.15.4", Aerospace conference, 2006 IEEE big sky, (Mar. 4-11, 2006), 1-8.
Bange, Joseph E, et al., "U.S. Appl. No. 11/101,196, filed Apr. 7, 2005", 19 pgs.
Bange, Joseph E, et al., "Implantable Medical Device Telemetry With Adaptive Frequency Hopping", U.S. Appl. No. 11/456,937, filed Jul. 12, 2006, 35 pgs.
Bange, Joseph E, et al., "Implantable Medical Device Telemetry With Periodic Frequency Hopping", U.S. Appl. No. 11/456,942, filed Jul. 12, 2006, 43 pgs.
Bange, Joseph E, et al., "System and Method for RF Wake-Up of Implantable Medical Device", U.S. Appl. No. 11/101,142, filed Apr. 7, 2005, 19 pgs.
Crow, B P, et al., "Investigation of the IEEE 802.11 medium access control (MAC) sublayer functions", Proceedings IEEE INFOCOM '97. Sixteenth Annual Joint Conference of the IEEE Computer and Communications Societies, vol. 1, (1997), 126-133.
Diffie, W., "The First Ten Years of Public-Key Cryptography", Proceedings of the IEEE, 76(5), (May 1988), 560-577.
Duflot, M., et al., "A formal analysis of bluetooth device discovery", International journal on software tools for technology transfer, 8 (6), (Jul. 5, 2006), 621-632.
Golmie, N., et al., "The Evolution of Wireless LANs and PANs -Bluetooth and WLAN coexistence: challenges and solutions", IEEE Personal Communications, 10(6), (Dec. 2003), 22-29.
Guidant, "Feature Sheet and Specifications: Zoom Latitude", Doc. No. C3-194-1005, (2005), 2 pgs.
Guidant, "Go Beyond the Wand", Doc. No. C3-107-0505, (2005), 2 pgs.
Guidant, "Think Beyond the Wand", Doc. No. C3-101-0505, (2005), 3 pgs.
Guidant, "What if you could ZIP through implants and follow ups?", Doc. No. C3-117-0505, (2005), 2 pgs.
Guidant, "What if your patient develops diaphragmatic stimulation?", Doc. No. 03-116-0505, (2005), 2 pgs.
Harney, Austin, et al., "Wireless Short-Range Devices: Designing a Global License-Free System for Frequencies <1 GHz", Analog Dialogue 40-03, (Mar. 2006), 1 pg.
Healy, S. J., et al., "System and Method for Providing Secure Exchange of Sensitive Information With an Implantable Medical Device", U.S. Appl. No. 10/801,150, filed Mar. 15, 2004, 30 pgs.
Katoozi, M., et al., "On-Demand Retransmission of Data With an Implantable Medical Device", U.S. Appl. No. 10/870,328, filed Jun. 17, 2004, 30 pgs.
Quiles, S., "U.S. Appl. No. 10/914,499, filed Aug. 9, 2004", 30 pgs.
Quiles, Sylvia, "U.S. Appl. No. 10/914,496, filed Aug. 9, 2004", 23 pgs.
Rawat, Prashant, et al., "U.S. Appl. No. 10/744,943, filed Dec. 22, 2003", 34 pgs.
Seeberger, M., "Dynamic Telemetry Link Selection for an Implantable Device", U.S. Appl. No. 10/914,638, filed Aug. 9, 2004.
Von Arx, J. A., et al., "A Telemetry Duty Cycle Management System for an Implantable Medical Device", U.S. Appl. No. 11/325,584, filed Jan. 4, 2006, 37 pgs.
Von Arx, Jeffrey, "U.S. Appl. No. 10/870,324, filed Jun. 14, 2004", 38 pgs.
Zhu, H., et al., "A survey of quality of service in IEEE 802.11 Networks", IEEE Wireless Communications, IEEE Service Center, Piscataway, NJ, US, 11(4), (Aug. 2004), 6-14 pgs.
Wikipedia, "SHA hash functions" <http://en.wikipedia.org/wiki/SHA> (1993), 8 pgs.
"U.S. Appl. No. 10/601,763, Non Final Office Action mailed Feb. 23, 2006", 9 pgs.
"U.S. Appl. No. 10/601,763, Notice of Allowance mailed Aug. 4, 2006", 8 pgs.
"U.S. Appl. No. 10/601,763, Response filed May 23, 2006 to Non Final Office Action mailed Feb. 23, 2006", 13 pgs.
"U.S. Appl. No. 10/601,763, Supplemental Notice of Allowability mailed Oct. 23, 2006", 4 pgs.

(56) References Cited

OTHER PUBLICATIONS

"U.S. Appl. No. 10/744,943, Non-Final Office Action mailed Mar. 19, 2010", 10 pgs.
"U.S. Appl. No. 10/744,943, Non-Final Office Action mailed Apr. 20, 2007", 8 pgs.
"U.S. Appl. No. 10/744,943, Non-Final Office Action mailed Aug. 1, 2006", 7 pgs.
"U.S. Appl. No. 10/744,943, Non-Final Office Action Mailed Aug. 7, 2009", 11 pgs.
"U.S. Appl. No. 10/744,943, Non-Final Office Action Mailed Oct. 28, 2008", 16 pgs.
"U.S. Appl. No. 10/744,943, Non-Final Office Action mailed Dec. 15, 2005", 7 pgs.
"U.S. Appl. No. 10/744,943, Notice of Allowance mailed Nov. 1, 2010", 7 pgs.
"U.S. Appl. No. 10/744,943, Response filed Feb. 1, 2007 to Non-Final Office Action mailed Aug. 1, 2006", 11 pgs.
"U.S. Appl. No. 10/744,943, Response filed Mar. 30, 2009 to Non Final Office Action mailed Oct. 28, 2008", 8 pgs.
"U.S. Appl. No. 10/744,943, Response filed May 15, 2006 to Non-Final Office Action mailed Dec. 5, 2005", 9 pgs.
"U.S. Appl. No. 10/744,943, Response filed Aug. 18, 2010 to Non Final Office Action mailed Mar. 19, 2010", 14 pgs.
"U.S. Appl. No. 10/744,943, Response filed Aug. 19, 2008 to Final Office Action mailed Feb. 21, 2008", 9 pgs.
"U.S. Appl. No. 10/744,943, Response filed Sep. 6, 2005 to Restriction Requirement mailed Aug. 3, 2005", 8 pgs.
"U.S. Appl. No. 10/744,943, Response filed Nov. 9, 2009 to Non Final Office Action mailed Aug. 7, 2009", 12 pgs.
"U.S. Appl. No. 10/744,943, Restriction Requirement mailed Aug. 3, 2005", 5 pgs.
"U.S. Appl. No. 10/801,070, 312 Amendment filed Apr. 11, 2007", 4 pgs.
"U.S. Appl. No. 10/801,070, Non Final Office Action mailed Feb. 6, 2006", 17 pgs.
"U.S. Appl. No. 10/801,070, Non Final Office Action mailed Jun. 16, 2006", 6 pgs.
"U.S. Appl. No. 10/801,070, Non-Final Office Action mailed Jun. 16, 2006", 6 pgs.
"U.S. Appl. No. 10/801,070, Non-Final Office Action mailed Feb. 6, 2006", 20 pgs.
"U.S. Appl. No. 10/801,070, Notice of Allowance mailed Jan. 12, 2007", 7 pgs.
"U.S. Appl. No. 10/801,070, Response filed Mar. 7, 2006 to Non Final Office Action mailed Feb. 6, 2006", 10 pgs.
"U.S. Appl. No. 10/801,070, Response filed Sep. 18, 2006 to Non Final Office Action mailed Jun. 16, 2006", 11 pgs.
"U.S. Appl. No. 10/801,070, Response filed Mar. 7, 2006 to Non-Final Office Action", 14 pgs.
"U.S. Appl. No. 10/801,070, Response filed Sep. 18, 2006 to Non Final Office Action mailed Jun. 16, 2006", 15 pgs.
"U.S. Appl. No. 10/914,499, Final Office Action mailed Jul. 20, 2010", 5 pgs.
"U.S. Appl. No. 10/914,641, Final Office Action dated Apr. 17, 2007", 10 pgs.
"U.S. Appl. No. 10/914,641, Final Office Action mailed Feb. 20, 2008", 9 pgs.
"U.S. Appl. No. 10/914,641, Final Office Action mailed Mar. 10, 2009", 10 pgs.
"U.S. Appl. No. 10/914,641, Final Office Action mailed Mar. 11, 2010", 11 pgs.
"U.S. Appl. No. 10/914,641, Final office action mailed Mar. 15, 2007", 10 pgs.
"U.S. Appl. No. 10/914,641, Non Final Office Action mailed Aug. 2, 2006", 9 pgs.
"U.S. Appl. No. 10/914,641, Non Final Office Action mailed Aug. 18, 2009", 11 pgs.
"U.S. Appl. No. 10/914,641, Non Final Office Action mailed Aug. 22, 2008", 9 pgs.
"U.S. Appl. No. 10/914,641, Non Final Office Action Mailed Aug. 31, 2007", 9 pgs.
"U.S. Appl. No. 10/914,641, Notice of Allowance dated Aug. 4, 2006", 8 pgs.
"U.S. Appl. No. 10/914,641, Notice of Allowance mailed Oct. 6, 2010", 5 pgs.
"U.S. Appl. No. 10/914,641, Response filed Jan. 2, 2007 to Non Final Office Action mailed Aug. 2, 2006", 9 pgs.
"U.S. Appl. No. 10/914,641, Response filed Jan. 18, 2007 to Non-Final Office Action", 21 pgs.
"U.S. Appl. No. 10/914,641, Response filed May 11, 2009 to Final Office Action mailed Mar. 10, 2009", 12 pgs.
"U.S. Appl. No. 10/914,641, Response filed May 18, 2010 to Final Office Action mailed Mar. 11, 2010", 11 pgs.
"U.S. Appl. No. 10/914,641, Response filed Jun. 10, 2009 to Advisory Action mailed Mar. 10, 2009", 11 pgs.
"U.S. Appl. No. 10/914,641, Response filed Jun. 16, 2006 to Restriction Requirement mailed May 16, 2006", 5 pgs.
"U.S. Appl. No. 10/914,641, Response filed Jul. 16, 2007 to Final Office Action mailed Mar. 15, 2007", 9 pgs.
"U.S. Appl. No. 10/914,641, Response filed Nov. 18, 2009 to Non Final Office Action mailed Aug. 18, 2009", 11 pgs.
"U.S. Appl. No. 10/914,641, Response filed Nov. 24, 2008 to Non Final Office Action mailed Aug. 22, 2008", 11 pgs.
"U.S. Appl. No. 10/914,641, Response filed Nov. 30, 2007 to Non Final Office Action mailed Aug. 31, 2007", 14 pgs.
"U.S. Appl. No. 10/914,641, Restriction Requirement mailed May 16, 2006", 5 pgs.
"U.S. Appl. No. 11/068,478, Advisory Action mailed Sep. 16, 2008", 3 pgs.
"U.S. Appl. No. 11/068,478, Corrected Notice of Allowance mailed Jun. 19, 2009", 4 pgs.
"U.S. Appl. No. 11/068,478, Response filed Nov. 3, 2008 to Advisory Action mailed Sep. 16, 2008", 17 pgs.
"U.S. Appl. No. 11/456,942, Advisory Action mailed May 7, 2009", 6 pgs.
"U.S. Appl. No. 11/456,942, Final Office Action mailed Mar. 10, 2009", 15 pgs.
"U.S. Appl. No. 11/456,942, Non-Final Office Action mailed Aug. 18, 2008", 15 pgs.
"U.S. Appl. No. 11/456,942, Notice of Allowance mailed Jul. 17, 2009", 13 pgs.
"U.S. Appl. No. 11/456,942, Response filed May 4, 2009 to Final Office Action mailed Mar. 10, 2009", 9 pgs.
"U.S. Appl. No. 11/456,942, Response filed Jun. 4, 2009 to Advisory Action mailed May 7, 2009", 10 pgs.
"U.S. Appl. No. 11/456,942, Response filed Nov. 18, 2008 to Non-Final Office Action mailed Aug. 18, 2008", 10 pgs.
"U.S. Appl. No. 11/640,552, Examiner Interview Summary mailed May 27, 2010", 4 pgs.
"U.S. Appl. No. 11/640,552, Examiner Interview Summary mailed Aug. 10, 2009", 3 pgs.
"U.S. Appl. No. 11/640,552, Final Office Action mailed Mar. 24, 2010", 8 pgs.
"U.S. Appl. No. 11/640,552, Non Final Office Action mailed May 11, 2009", 8 pgs.
"U.S. Appl. No. 11/640,552, Response filed Jun. 24, 2010 to Final Office Action mailed Mar. 24, 2010", 9 pgs.
"U.S. Appl. No. 11/738,942, Non Final Office Action mailed Jan. 20, 2010", 8 pgs.
"U.S. Appl. No. 11/738,942, Non Final Office Action mailed Jun. 9, 2009", 14 pgs.
"U.S. Appl. No. 11/738,942, Notice of Allowance mailed Jun. 17, 2010", 8 pgs.
"U.S. Appl. No. 11/738,942, Preliminary Amendment filed Apr. 23, 2007", 6 pgs.
"U.S. Appl. No. 11/738,942, Response filed Apr. 20, 2010 to Non Final Office Action mailed Jan. 20, 2010", 10 pgs.
"U.S. Appl. No. 11/738,942, Response filed Sep. 16, 2009 to Non Final Office Action mailed Jun. 9, 2009", 9 pgs.
"U.S. Appl. No. 12/004,892, Notice of Allowance mailed Jun. 21, 2012", 5 pgs.

(56) References Cited

OTHER PUBLICATIONS

"U.S. Appl. No. 12/145,343, Final Office Action mailed Mar. 8, 2011", 9 pgs.
"U.S. Appl. No. 12/145,343, Non-Final Office Action mailed Oct. 26, 2010", 10 pgs.
"U.S. Appl. No. 12/145,343, Response filed Jan. 25, 2011 to Non Final Office Action mailed Oct. 26, 2010", 9 pgs.
"U.S. Appl. No. 12/145,343, Response filed May 9, 2011 to Final Office Action mailed Mar. 8, 2011", 9 pgs.
"U.S. Appl. No. 12/145,343, Response filed Sep. 14, 2010 to Restriction Requirement mailed Aug. 26, 2010", 8 Pgs.
"U.S. Appl. No. 12/145,343, Restriction Requirement mailed Aug. 26, 2010", 7 pgs.
"U.S. Appl. No. 12/684,303, Response filed Jun. 13, 2011 to Non-Final Office Action mailed Apr. 5, 2011", 10 pgs.
"U.S. Appl. No. 12/950,359, Notice of Allowance mailed Jun. 23, 2011", 7 pgs.
"European Application Serial No. 02799254.4, Communication mailed Oct. 2, 2006", 4 pgs.
"European Application Serial No. 02799254.4, Response filed Feb. 15, 2010 to Office Action mailed Sep. 23, 2009", 12 pgs.
"European Application Serial No. 02799254.4, Response filed Apr. 2, 2007 to Communication mailed Oct. 2, 2006", 18 pgs.
"European Application Serial No. 03709003.2, Office Action mailed Jul. 27, 2010", 6 pgs.
"European Application Serial No. 03709003.2, Response filed Jan. 27, 2011 to office action mailed Jul. 27, 2010", 10.
"European Application Serial No. 05732873.4, Office Action mailed Nov. 17, 2011", 4 pgs.
"European Application Serial No. 05732873.4, Response filed Jan. 26, 2012 to Office Action mailed Nov. 17, 2011", 11 pgs.
"European Application Serial No. 05783882.3, Response filed Oct. 22, 2009 to Communication mailed Jun. 16, 2009", 7 pgs.
"International Application No. PCT/US2004/019902, International Search Report dated Dec. 6, 2004", 4 pgs.
"International Application No. PCT/US2004/019902, Written Opinion dated Dec. 6, 2004", 6 pgs.
"International Application No. PCT/US2005/008521, International Preliminary Report on Patentability mailed Sep. 28, 2006", 13 pgs.
"International Application No. PCT/US2005/008521, International Search Report and Written Opinion mailed Oct. 11, 2005", 19 pgs.
"International Application No. PCT/US2005/008521, International Search Report mailed Oct. 11, 2005", 19 pgs.
"International Application No. PCT/US2005/008521, Invitation to Pay Additional Fees and Partial International Search Report mailed Jul. 29, 2005", 7 pgs.
"Japanese Application No. 2004-527861, Notice of Allowance mailed Jun. 16, 2010", 3 pgs.
"Japanese Application Serial No. 2006-517513, Notice of Allowance mailed Jan. 21, 2011", 3 pgs.
"Japanese Application Serial No. 2006-517513, Office Action mailed Jan. 18, 2010", (w/ English Translation), 5 pgs.
"Japanese Application Serial No. 2006-517513, Office Action mailed Oct. 12, 2010", 1 pg.
"Japanese Application Serial No. 2006-517513, Response filed Apr. 19, 2010 to Office Action mailed Jan. 18, 2010", (w/ English Translation of Amended Claims), 41 pgs.
"Japanese Application Serial No. 2006-517513, Response filed Dec. 13, 2010 to Office Action Sep. 14, 2010", (w/ English Translation of Amended Claims), 16 pgs.
"Japanese Application Serial No. 2007-507458, Notice of Allowance mailed Feb. 14, 2011", 3 pgs.
"Japanese Application Serial No. 2007-525695, Office Action mailed Feb. 3, 2011", (w/ English Translation), 5 pgs.
"Japanese Application Serial No. 2007-525695, Response filed Apr. 20, 2011 to Non Final Office Action mailed Feb. 3, 2011", (w/ English Translation of Amended Claims), 10 pgs.
"Japanese Application Serial No. 2007-525697, Response filed Jun. 8, 2011 to Office Action mailed Apr. 19, 2011", (w/ English Translation of Amended Claims), 13 pgs.
Hammond, E., "Perspectives on Implementation of Administrative Simplification Provisions of P.L. 104-191", National Committee on Vital and Health Statistics, Subcommittee on Health Data Needs, Standards and Security, (Feb. 11, 1997), 4 pgs.
Healy, S. J., et al., "Cryptographic Authentication for Telemetry With an Implantable Medical Device", U.S. Appl. No. 10/801,070, filed Mar. 15, 2004, 38 pgs.
Quiles, S., "Secure Remote Access for an Implantable Medical Device", U.S. Appl. No. 10/914,641, filed Aug. 9, 2004, 41 pgs.
Von Arx, J., et al., "System and Method for Securely Authenticating a Data Exchange Session With an Implantable Medical Device", U.S. Appl. No. 10/800,806, filed Mar. 15, 2004, 47 pgs.
Zarlink Semiconductor, "Medical Implantable RF Transceiver", (2005), 40 pgs.

* cited by examiner

SYSTEM AND METHOD FOR RF WAKE-UP OF IMPLANTABLE MEDICAL DEVICE

CROSS-REFERENCE TO RELATED APPLICATIONS

This application is a continuation of U.S. application Ser. No. 13/218,672, filed Aug. 26, 2011, is now issued U.S. Pat. No. 8,326,424, which is a continuation of U.S. application Ser. No. 12/102,480, filed Apr. 14, 2008, now issued as U.S. Pat. No. 8,024,043, which is a continuation of U.S. application Ser. No. 11/101,142, filed Apr. 7, 2005, now issued as U.S. Pat. No. 7,359,753, which claims the benefit of U.S. Provisional Application No. 60/560,171, filed on Apr. 7, 2004, under 35 U.S.C. §119(e), which are hereby incorporated by reference.

FIELD OF THE INVENTION

This invention pertains to implantable medical devices such as cardiac pacemakers and implantable cardioverter/defibrillators. In particular, the invention relates to a system and method for implementing telemetry in such devices.

BACKGROUND

Implantable medical devices, including cardiac rhythm management devices such as pacemakers and implantable cardioverter/defibrillators, typically have the capability to communicate data with a device called an external programmer via a radio-frequency telemetry link. One use of such an external programmer is to program the operating parameters of an implanted medical device. For example, the pacing mode and other operating characteristics of a pacemaker are typically modified after implantation in this manner. Modern implantable devices also include the capability for bidirectional communication so that information can be transmitted to the programmer from the implanted device. Among the data that may typically be telemetered from an implantable device are various operating parameters and physiological data, the latter either collected in real-time or stored from previous monitoring operations.

Telemetry systems for implantable medical devices utilize radio-frequency (RF) energy to enable bidirectional communication between the implantable device and an external programmer. An exemplary telemetry system for an external programmer and a cardiac pacemaker is described in U.S. Pat. No. 4,562,841, issued to Brockway et al. and assigned to Cardiac Pacemakers, Inc., the disclosure of which is incorporated herein by reference. A radio-frequency carrier is modulated with digital information, typically by amplitude shift keying where the presence or absence of pulses in the signal constitute binary symbols or bits. The external programmer transmits and receives the radio signal with an antenna incorporated into a wand that can be positioned in proximity to the implanted device. The implantable device also generates and receives radio signals by means of an antenna, typically formed by a wire coil wrapped around the periphery of the inside of the device casing. Most conventional radio-frequency telemetry systems used for implantable medical devices such as cardiac pacemakers utilize inductive coupling between the antennas of the implantable device and an external programmer in order to transmit and receive RF signals. Because the induction field produced by a transmitting antenna falls off rapidly with distance, such systems require close proximity between the implantable device and a wand antenna of the external programmer in order to work properly, usually on the order of a few inches. This requirement is an inconvenience for a clinician and limits the situations in which telemetry can take place.

Wireless radio-frequency communication over greater distances requires the use of far-field telemetry. Communication using far-field radiation can take place over much greater distances, which makes it more convenient to use an external programmer. Also, the increased communication range makes possible other applications of the telemetry system such as remote monitoring of patients and communication with other types of external devices such as network access points. In order for a substantial portion of the energy delivered to an antenna to be emitted as far-field radiation, the wavelength of the driving signal should not be very much larger than the length of the antenna. Far-field radio-frequency communications with an antenna of a size suitable for use in an implantable device therefore requires a carrier in the frequency range of between a few hundred MHz to a few GHz. Active transmitters and receivers for this frequency range require special RF components (typically including SiGe or GaAs semiconductor devices) that consume a significant amount of power (typically tens of milliwatts). Implantable medical devices, however, are powered by a battery contained within the housing of the device that can only supply a limited amount of continuous power before it fails. When the battery fails in an implantable device, it must be replaced which necessitates a re-implantation procedure. Power conservation is thus an important design objective in wireless telemetry systems for implantable medical devices.

SUMMARY

The present invention relates to a telemetry system for enabling radio-frequency (RF) communications between an implantable medical device and an external device in a manner which reduces the power requirements of the implantable device. In accordance with the invention, the external device is programmed to transmit a data segment containing a repeating sequence of special wakeup characters in order to establish a communications session with the implantable device. The implantable device is programmed to power up its transmitter and receiver for a specified time window at periodic intervals defined by the wakeup timer and wait for receipt of one of the special wakeup characters transmitted by the external device. The implantable device maintains its transmitter and receiver in a powered-up state upon receipt of a special character and for as long as consecutive special wakeup characters continue to be received, to transmit an acknowledge signal to the external device upon receipt of at least one character other than a special wakeup character, and then to wait a specified period of time for a response from the external device. The external device and the implantable device then attempt to establish a communications session when a response to the acknowledge signal is received by the implantable device.

DETAILED DESCRIPTION

Figure 1:
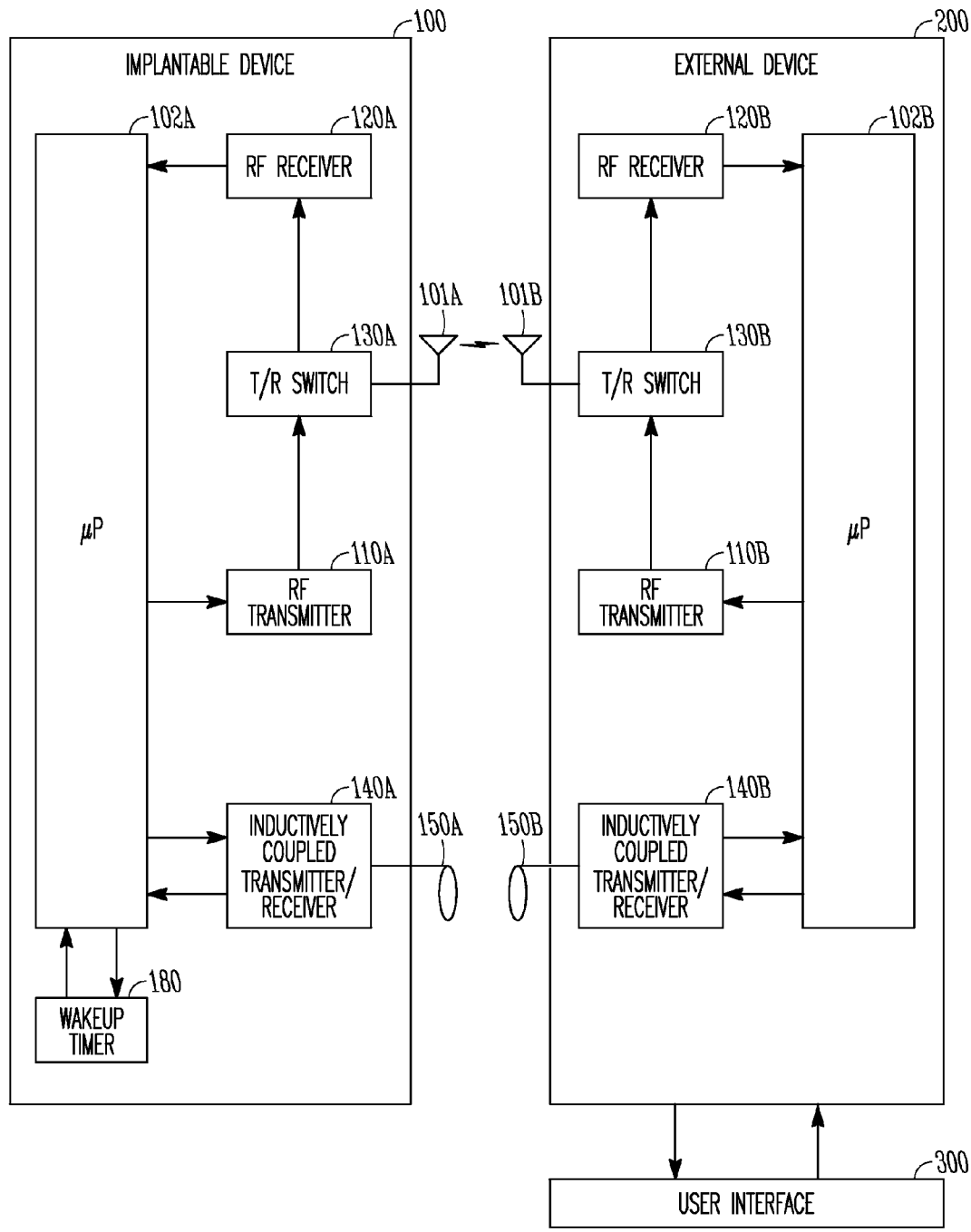
FIG. 1 is a block diagram of a telemetry system for an implantable device and an external device.

The present invention is a system and method for providing far-field RF telemetry between an implantable medical device and an external device in which power consumption by the implantable device is lessened by managing the duty cycle of the RF transmitting and receiving components. Long-range RF telemetry circuitry (i.e., the transmitter and receiver) typically requires power on the order of tens of milliwatts in order to operate. Implantable cardiac devices in use today, on the other hand, are usually designed to operate with average power in the microwatt range. This means that the RF telemetry circuitry must be duty cycled down in order to meet the power budget of such devices. Previous examples of duty cycling for implantable devices are described in U.S. Pat. No. 5,342,408 and U.S. patent application Ser. No. 10/025,223, entitled "A TELEMETRY DUTY CYCLE MANAGEMENT SYSTEM FOR AN IMPLANTABLE MEDICAL DEVICE", presently assigned to Cardiac Pacemakers, Inc., and hereby incorporated by reference.

The RF telemetry circuitry of an implantable device can either be powered up or down, referred to as awake and sleep states, respectively. Duty cycling of the implantable device's RF telemetry circuitry can be implemented by a wakeup timer which defines periodic wakeup intervals at which the implantable device powers up its RF circuitry and listens for a transmission from an external device for a specified period of time, referred to as a wakeup window. Upon acknowledging the transmission from the external device, a communications session can be established by a handshaking protocol, and data can then be transferred between the devices. In order to minimize power consumption, it is desirable for the RF circuitry of the implantable device to be powered up for as short a time as possible at each wakeup interval while still being able to reliably recognize session requests from the external device. If the implantable device recognizes a session request from the external device during its wakeup window, it remains awake long enough to establish a communications session with the external device; otherwise, the implantable device returns to a sleep state until the next wakeup interval occurs.

In accordance with the present invention, the external device is programmed to transmit a data frame containing a repeating sequence of special wakeup characters when it is desired to establish a communications session with the implantable device. The implantable device is programmed to power up its transmitter and receiver for a specified wakeup window at periodic intervals defined by its wakeup timer and wait for receipt of one of the special wakeup characters transmitted by the external device. The implantable device maintains its transmitter and receiver in a powered-up state upon receipt of a special character and for as long as consecutive special wakeup characters continue to be received, and transmits an acknowledge signal to the external device upon receipt of at least one character other than a special wakeup character. After transmitting the acknowledge signal, the implantable device then waits a specified period of time for a response from the external device. When a response to the acknowledge signal is received by the implantable device, the external device and the implantable device are programmed to establish a communications session by a handshaking protocol. During a communications session, the RF transmitter and receiver of the implantable device may then either be maintained in the powered-up state for the duration of the communications session or powered down at prescribed intervals according to a defined protocol.

As described in detail below, the wakeup scheme may be designed to work in the context of a medium access control (MAC) protocol by which network participants contend for access to the wireless medium. Also, in one embodiment, the implantable device and the external device communicate by a transmission code which provides a DC balanced data stream such as 8b/10b. Such bit balanced data streams are advantageous in RF communications. In order for the special wakeup character to be invariant, the special wakeup character may be selected as a bit balanced sequence which is not changed by the transmission code.

In another particular embodiment, the external device is a remote monitor (RM) which operates to periodically collect data from the implantable device. The remote monitor may thus include a wakeup timer and be programmed to transmit a plurality of special wakeup characters to the implantable device in an attempt to establish a communications session at periodic intervals as defined by its wakeup timer. After the implantable device is awoken by the special wakeup characters, a communications session is established in which the implantable device transmits whatever data it has to the RM. If the implantable device has no data to transmit, however, the communications session is terminated almost immediately after being established. Such empty communications sessions still impose an energy cost upon the implantable device, however, due to the time it takes for the implantable device to wake up, establish a communications session with the RM, indicate that there is nothing to download, and then terminate the session. The total duty cycle of the RF circuitry in the implantable device is thus a function of both its own wakeup interval and the intervals at which the RM attempts to wake up the implantable device. In order to lessen power consumption by the implantable device, therefore, it is desirable for the intervals at which the RM attempts to wake up the implantable device to be such that the number of empty communications sessions is minimized. The remote monitor may thus be further programmed to adjust the periodic intervals at which it transmits a plurality of special wakeup characters to the implantable device in accordance with when previous successful communications sessions have been established such that data was collected. In one particular embodiment, the remote monitor is programmed to establish a communications session and collect data from the implantable device on a daily basis and further programmed to adjust the periodic intervals at which it attempts to wake up the implantable device in accordance with the time of day at which past successful communications sessions were established. In order to be able to respond to an episode, the remote monitor may also be programmed to transmit a plurality of special wakeup characters to the implantable device for establishing a communications session when a user command is received via a user interface.

1. Exemplary Hardware Components

FIG. 1 shows the primary telemetry components of an external device 200 and an implantable medical device 100. In this functional block diagram, the components are shown as being identical in each device. In this exemplary embodiment, the external device and the implantable device are microprocessor-based devices each having a controller 102a or 102b that includes a microprocessor and memory for data and program storage that supervises overall device operation as well as telemetry. Code executed by the controller also implements the duty cycle management schemes to be described below. The implantable device 100 may be a cardiac rhythm management device such as a pacemaker or implantable cardioverter/defibrillator, while the external device 200 may be an external programmer or a data-gathering device such as remote monitor. A user interface 300 (e.g., a keyboard and monitor) enables a user such as a clinician to direct the operation of the external device.

A long-range RF receiver 120a or 120b and a long-range RF transmitter 110a or 110b are interfaced to the microprocessor 102*a* or 102*b* in the implantable device and the external device, respectively. Also in each device, the transmitter and receiver are coupled to an antenna 101*a* or 101*b* through a transmit/receive switch 130*a* or 130*b*. The transmit/receive switches 130*a* and 130*b* are controlled by the microprocessor and either passes radio-frequency signals from the transmitter to the antenna or from the antenna to the receiver. To effect communications between the devices, a radio-frequency carrier signal modulated with digital data is transmitted wirelessly from one antenna to the other. A demodulator for extracting digital data from the carrier signal is incorporated into each receiver, and a modulator for modulating the carrier signal with digital data is incorporated into each transmitter. The interface to the controller for the RF transmitter and receiver in each device enables data transfer. The implantable device also incorporates a means by which the controller can power up or power down the RF receiver and/or transmitter in order to manage duty cycles in the manner described below. A wakeup timer 180 for defining the RF duty cycle is also shown for the implantable device, and this timer can either be implemented in code executed by the controller or can be discrete components. FIG. 1 also shows an inductively coupled transmitter/receiver 140*a* or 140*b* and antenna 150*a* or 150*b* for the implantable and external devices by which communication may take place without concern for power consumption when the two devices are in close physical proximity to one another.

2. Description of Specific Embodiments

Figure 2:
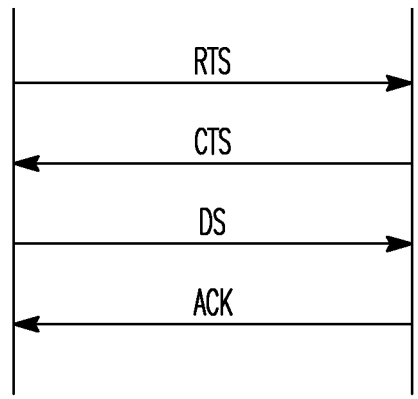
FIG. 2 illustrates a handshaking protocol for collision avoidance.

A wireless telemetry system for implantable medical devices is generally a multiple access network in which a number of network participants share the available bandwidth of the wireless medium. A medium access control (MAC) protocol may be defined which allows each network participant to acquire exclusive access to the medium before transmitting data to an intended recipient. A collision is said to occur when two or more participants attempt to transmit at the same time. In certain networks, collisions may be detected by the sender listening to the medium when a transmission is initiated to determine if other network activity is present. If a collision is detected, the sender ceases transmitting and waits for a random or defined period before trying again. Most wireless transceivers operate in a half-duplex mode, however, and cannot simultaneously transmit and listen for ongoing network activity. MAC protocols for wireless networks therefore typically use out-of-band signaling or a handshaking protocol to minimize the probability of a collision occurring. In an example of the latter type of protocol, a four-way RTS-CTS-DS-ACK exchange as illustrated by FIG. 2 is used to avoid collisions. A network participant who desires to send a message to a particular recipient first transmits a request-to-send (RTS) frame and waits a defined period of time for a clear-to-send (CTS) frame from the intended recipient. All network participants who hear either of the RTS or CTS frames defer their transmissions. Upon receiving the CTS response, the sender can assume that the medium has been exclusively acquired and can then begin transmission of a data segment (DS) to the recipient. If the data is received without errors, the recipient responds with an acknowledge (ACK) frame which frees the medium for access by another participant. The present invention, in various embodiments, may work in the context of any of the medium access control protocols discussed above.

a. Exemplary Wakeup Scheme

Figure 3:
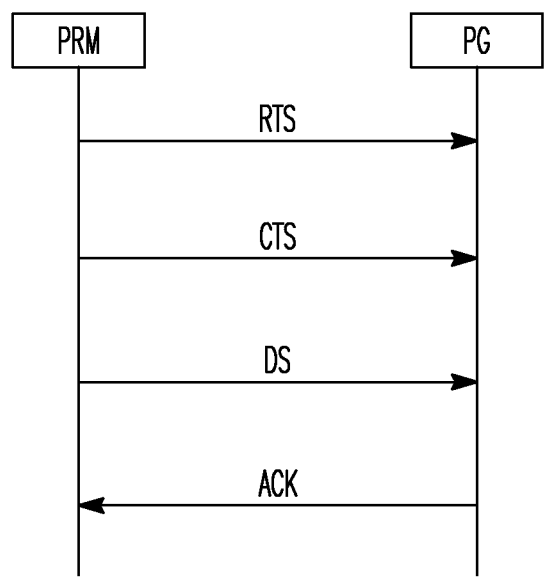
FIG. 3 illustrates a wakeup scheme in accordance with the invention.

A particular embodiment of the invention will now be described with reference to an external programmer or remote monitor (PRM/RM) and an implantable device (referred to as a pulse generator or PG). In this embodiment, the wakeup process works within the framework of a handshaking collision avoidance scheme as described above. In such a scheme, a network participant may transmit a so-called universal broadcast to all other participants in the network by transmitting an RTS-CTS-DS-ACK sequence. The PRM/RM transmits the RTS and CTS frames to cause other participants to defer their transmissions, transmits a data segment DS, and then transmits an ACK frame to release the medium. The wakeup process is illustrated by FIG. 3 and is similar to a universal broadcast with the exception that the PG provides the ACK frame instead of the PRM/RM. The PRM/RM sends out the messages RTS, CTS, and DS using the universal access code. The length of the DS message is set to a large number (e.g., 256 bytes), and the entire data portion of the message area is set to a repeating sequence of a special 10-bit character reserved solely for use as a wakeup indicator. (As described below, the wakeup indicator may be a special 8b/10b character.) The PG wakes up periodically (e.g., every 20-30 seconds) and listens for a very short interval to receive the wakeup special character. This short wakeup interval needs to be on the order of slightly longer than twenty bits after the PG's RF receiver has stabilized so that at least one entire 10-bit special character can be received. It is important to note that any normal preamble that is designed to get the PG receiver to its steady state of operation will not be present during the wakeup. An additional time is therefore required, on the order of an additional 10 bits above the standard 20 bits for a total of 30 bits. This means that the minimum wakeup time in this embodiment is 50 bits (10+20+20), which is 440 microseconds at a modulation rate of 113.7 Kbps. The projections below are based on a margin above this of 500 μs allowing for a 6-bit margin. If one wakeup special character is received, then the PG will stay awake long enough to receive several more wakeup special characters. If several wakeup special characters are received, the PG stays awake until it no longer receives special characters. After two consecutive non-special characters (e.g., these could be the CRC values of the DS frame), the PG responds with an ACK frame and will now stay awake for an extended period of time. The PRM having successfully received this ACK message will then proceed to perform a discovery process which will contend for message traffic within the protocol framework in order to establish a communications session with the PG.

In the wakeup scheme just described, a problem may arise if two PG's are in range of the PRM/RM when the wakeup sequence is transmitted. If both PG's wake up and respond to the wakeup sequence with an ACK frame, a collision will occur. In a further modification of the scheme, the PRM/RM may therefore be programmed to monitor the RF signal strength after transmission of the wakeup sequence during the expected ACK response time and proceed with the discovery process if there is found to be some RF activity.

An advantage of the wakeup scheme described above is that the PRM/RM is able to quickly establish a communications session with the PG on demand. The PG will be woken up within 20 seconds if the PG wakes up every 20 seconds and wakes up when a special character is being transmitted. (The probability that the PG will be awoken within that time increases with the length of the sequence of repeating special characters transmitted by the PRM/RM.) At the same time, the PG is subjected to a very low duty cycle which lessens the power requirements of operating a far-field RF telemetry system to acceptable levels. For example, an exemplary implantable cardiac rhythm management device may operate at an average current draw on the order of 22 microamps and is designed to last 6 years before a battery replacement is needed. This means that each 305 nanoamps of current draw costs the device one month in longevity. When the RF circuitry is powered up, its current draw is on the order of 4 milliamps. If the device wakes up every 20 seconds and remains powered up for 500 microseconds, the duty cycle is 1/40,000. The average current due to wake ups (but not, of course, including the current necessary for actually performing telemetry) is then (4 mA) (1/40,000)=100 nanoamps, resulting in a longevity cost to the device of just over a week.

b. Choice of Special Wakeup Character

In an embodiment where a DC balanced coding scheme such as 8b/10b is employed, it is desired to know a priori that the wakeup special character is always going to have one value independent of the running disparity (RD) of the 8b/10b encoding. The first step in achieving this goal is to choose a wakeup preamble from the set of valid special characters that is bit balanced. There are 7 such codes that have exactly 5 ones and 5 zeros. Codes that are bit balanced do not change the running disparity after transmission so that successive transmission would be identical values avoiding the inversion that occurs on non-bit balanced codes. The second step is to determine what the initial running disparity is when the data portion of the DS message is sent. Since this message is predetermined, it is a simple matter to determine the running disparity. The RD has an initial negative value (RD−) and starts with the first byte of the access code. The RD is then computed after each of the 8b/10b conversions. The RD at the start of the data portion is then the RD after the two universal access code bytes, the command byte, and the length byte. The proposal for wakeup special character and universal access codes is to choose two of the 7 bit-balanced valid special characters. The values are chosen as:

| Code | Special code name | RD− | RD+ |
|---|---|---|---|
| Universal Access Code 1: | K28.0 | 0011110100 | 1100001011 |
| Universal Access Code 2: | K28.4 | 0011110010 | 1100001101 |
| Wakeup Special Code: | K29.7 | 1011101000 | 1011100111 |

The choice of the RD− K28.0 and K28.4 codes are used as the universal access code. After transmission, the RD remains negative. The command byte and length byte are next to be transmitted. The command and length bytes depend on the value of the DS command code (3) and the length. Using a length of 256 bytes (0x100) gives a command byte of 0x31 and a length byte of 0x00 (The least significant two bits of the command are the most significant bits of the length). The 0x31 command byte then becomes the 8b/10b code of D17.1 that is also bit balanced so the RD remains negative. The 0x00 length byte is the 8b/10b code of D0.0 which converts to 1001110100, again this code is bit balanced so the RD remains negative. Now the wakeup special code K29.7 can be transmitted containing the RD− code of 1011101000 repeatedly since the RD does not change. The CRC can take on its normal value and does not need to be considered here since it does not affect the RD of the data portion. Note that the alignment pattern is the 8b/10b code K28.5 (001111 1010) since it is the comma character.

Although the invention has been described in conjunction with the foregoing specific embodiments, many alternatives, variations, and modifications will be apparent to those of ordinary skill in the art. Such alternatives, variations, and modifications are intended to fall within the scope of the following appended claims.

What is claimed is:

1. A telemetry system for enabling wireless communications between an implantable medical device and an external remote monitor (RM), comprising:
a wireless transmitter, a wireless receiver, and a controller incorporated into each of the implantable medical device and the RM;
a wakeup timer incorporated into the implantable device;
wherein the transmitter and receiver of the implantable device are interfaced to the controller to enable the transmitter and receiver to be independently powered up or down;
wherein the RM is programmed to transmit a data segment containing a repeating sequence of special wakeup characters in order to establish a wireless communications session with the implantable device;
wherein the implantable device is configured to:
power up its receiver for a specified time window at periodic intervals to wait for receipt of a special wakeup character transmitted by the RM;
maintain its receiver and place its transmitter in a powered-up state upon receipt of the special character and for as long as consecutive special wakeup characters continue to be received; and
transmit an acknowledge signal upon receipt of at least one character other than a special wakeup character; and
wherein the RM is configured to:
establish a communications session with the implantable device when a response to the acknowledge signal is received by the implantable device; and
adjust a periodic interval at which the RM transmits the special wakeup characters to the implantable device according to when previous successful communications sessions have been established.

2. The system of claim 1, wherein implantable medical device transmitter includes a modulator configured to modulate a carrier signal with data, and wherein the modulator is placed in a powered up state upon receipt of the special wakeup character received from the RM.

3. The system of claim 1, wherein the at least one character other than the special wakeup character includes a collision avoidance message.

4. The system of claim 3, wherein the collision avoidance message includes a request-to-send message and a clear-to-send message.

5. The system of claim 1, wherein the RM defers transmission of the special wakeup character when the RM detects wireless communication activity.

6. The system of claim 1, wherein the RM is configured to perform a discovery process to contend for message traffic upon receiving the acknowledge signal from the implantable device.

7. The system of claim 6, wherein the RM is configured to monitor wireless communication signal strength during an expected acknowledge response time and perform the discovery process when communication activity is detected during the expected acknowledge response time.

8. The system of claim 1, wherein the implantable medical device receiver includes a demodulator configured to extract the special wakeup character from a carrier signal, and wherein the implantable medical device is configured to power up the demodulator for the specified time window.

9. The system of claim 8, wherein a duration of the specified time window provides for both stabilization of the implantable device receiver and demodulation of two special wakeup characters.

10. The system of claim 1, wherein the implantable medical device includes an inductive transmitter and an inductive receiver separate from the wireless transmitter and wireless receiver.

11. A method comprising:
wirelessly transmitting a data segment containing a repeating sequence of special wakeup characters by an external remote monitoring device (RM) in order to establish a wireless communications session with an implantable medical device;
powering up a receiver of the implantable medical device for a specified time window at periodic intervals to wait for receipt of a special wakeup character transmitted by the RM, wherein the implantable medical device maintains the receiver and places a transmitter in a powered-up state upon receipt of a special character and for as long as consecutive special wakeup characters continue to be received;
transmitting, by the implantable medical device, an acknowledge signal upon receipt of at least one character other than a special wakeup character;
establishing a communications session with the implantable medical device when a response to the acknowledge signal is received by the implantable device; and
adjusting, by the RM, a periodic interval at which the RM transmits the special wakeup characters to the implantable medical device according to when previous successful communications sessions have been established.

12. The method of claim 11, wherein transmitting by the implantable medical device includes modulating a carrier signal with data, and wherein the method includes the implantable device placing the modulator in a powered up state upon receipt of the special wakeup character.

13. The method of claim 11, wherein transmitting an acknowledge signal includes transmitting, by the implantable medical device, the acknowledge signal upon receipt of a collision avoidance message.

14. The method of claim 13, wherein transmitting the acknowledge signal includes transmitting, by the implantable medical device, the acknowledge signal upon receipt of a request-to-send message and a clear-to-send message.

15. The method of claim 11, including deferring, by the RM, transmission of the special wakeup character when the RM detects wireless communication activity.

16. The method of claim 11, including performing, by the RM, a discovery process to contend for message traffic upon receiving the acknowledge signal from the implantable medical device.

17. The method of claim 16, including:
monitoring, by the RM, wireless communication signal strength during an expected acknowledge response time, and
wherein performing the discovery process includes performing the discovery process when communication activity is detected during the expected acknowledge response time.

18. The method of claim 11, including:
demodulating, by the implantable medical device, the special wakeup character from a carrier signal, and
wherein powering up the receiver included powering up the demodulator for the specified time window.

19. The method of claim 18, wherein powering up the receiver includes powering up, by the implantable medical device, the receiver and demodulator for a specified time window having a duration that allows for both stabilization of the implantable device receiver and demodulation of two special wakeup characters by the demodulator.

20. The method of claim 11, wherein the special wakeup character of the plurality of special wakeup characters includes a sequence of direct current (DC) balanced bits.

* * * * *